(12) United States Patent
Poncelet et al.

(10) Patent No.: US 9,464,314 B2
(45) Date of Patent: Oct. 11, 2016

(54) FRAGMENTING DNA SEQUENCES LONGER THAN 10,000 BP USING ULTRASONICATION

(75) Inventors: Dominique Poncelet, Tongeren (BE); Irina Panteleeva, Vaux-Sous-Chevremont (BE); Kazuo Ito, Kanagawa-ken (JP); Didier Allaer, Villers le Bouillet (BE)

(73) Assignee: DIAGENODE S.A., Liege (BE)

( * ) Notice: Subject to any disclaimer, the term of this patent is extended or adjusted under 35 U.S.C. 154(b) by 750 days.

(21) Appl. No.: 13/447,606

(22) Filed: Apr. 16, 2012

(65) Prior Publication Data

US 2012/0264228 A1    Oct. 18, 2012

(30) Foreign Application Priority Data

Apr. 15, 2011 (EP) .................................... 11162716

(51) Int. Cl.
*G01N 1/44* (2006.01)
*C12Q 1/68* (2006.01)

(52) U.S. Cl.
CPC ............ *C12Q 1/6806* (2013.01); *Y10T 436/25* (2015.01)

(58) Field of Classification Search
CPC .......... C12Q 1/6806; C12Q 2523/301; G01N 1/286; B01J 19/10; Y10T 436/25
See application file for complete search history.

(56) References Cited

U.S. PATENT DOCUMENTS 3,596,883 A * 8/1971 Brech ............................ 366/115
4,963,477 A * 10/1990 Tchen .............................. 435/5

FOREIGN PATENT DOCUMENTS

WO    WO9303150 A1    2/1993

OTHER PUBLICATIONS

Grokhovsky, S.E., "Specificity of DNA cleavage by ultrasound," Molecular Biology, Kluwer Academic Publishers—Plenum Publishers, NE, vol. 40, No. 2, Mar. 1, 2006, pp. 276-283.
Larguinho, Miguel, et al., "Development of a fast and efficient ultrasonic-based strategy for DNA fragmentation," Talanta, vol. 81, No. 3, May 2010, pp. 881-886.
Sambrook, J., et al., "Fragmentation of DNA by Sonication," Cold Spring Harbor Protocols, vol. 2006, Jan. 1, 2006, pp. E-ARTICLE, XP009118981.
Rageh M.M., El-Lakkani A., et al., "Effect of high power ultrasound on aqueous solution of DNA," International Journal of Physical Sciences, vol. 4, 2009, pp. 63-68.
A.W. Davis and D.R. Phillips, "A Defined Molecular-Weight Distribution of Deoxyribonucleic Acid after Extensive Sonication," Biochem. J. (1978) 173, pp. 179-183.
European Search Report, Application No. EP11162716, Jun. 30, 2011, 2 pages.
Written Opinion, Application No. EP11162716, Jun. 30, 2011, 3 pages.

(Continued)

*Primary Examiner* — Christopher A Hixson
(74) *Attorney, Agent, or Firm* — The Marbury Law Group, PLLC

(57) ABSTRACT

A method of fragmenting a DNA sequence having a starting size of at least 10000 base pair into fragments having a mean size smaller than or equal to 1300 bp, wherein the DNA sequence is put in a solution, the solution comprising the DNA sequence is put in a container and the container is placed in a liquid bath which is subjected to the action of ultrasound waves such that the ultrasound waves travel through the liquid bath to excite the container and the solution so as to shear the DNA sequence, and wherein the ultrasound waves have a frequency falling in the range between 28 kHz and 80 kHz.

20 Claims, 8 Drawing Sheets

(56) References Cited

OTHER PUBLICATIONS

"Heat systems ultrasonic w-385 processor w/ C3 converter", http://fs.bookpawnshop.com/H/Heat-systems-ultrasonic-w-385-processor-w-C3-converter, pp. 1-2.
"Analytical Equipments", PCi Analytics, www.pcianalytics.in, pp. 1-2.
Sonicator, "Ultrasonic Liquid Processors", QSonica Sonicators, http://www.sonicator.com/20-sonicators, pp. 1-27.
Birren, et al., "Random Fragmentation by Sonication," Cold Spring Harbor Laboratory Press, Genome Analysis, vol. 1, Chapter 5, pp. 418-420, (1997).
Misonix Incorporated, "Sonicator, Ultrasonic Liquid Processor Operation manual", Models XL2020, XL2015 and XL2010, 44 pages, (1990).

* cited by examiner

FRAGMENTING DNA SEQUENCES LONGER THAN 10,000 BP USING ULTRASONICATION

RELATED APPLICATIONS

This application claims the priority benefit under 35 U.S.C. §119 of European Application No. 11162716.2, filed on Apr. 14, 2011, which is incorporated herein by reference in its entirety.

The present invention relates to methods and apparatuses for fragmentation of DNA, in order to fragment a larger DNA sequence into sequence fragments of smaller size. In particular, the present invention relates to the fragmentation of DNA by shearing using ultrasound waves, also referred to as sonication.

It has long been known to use ultrasound for creating focused mechanical stress to rupture cell walls, e.g. from GB 1363934 and U.S. Pat. No. 4,874,137. The ultrasound waves pass through the sample, expanding and contracting liquid. During expansion, molecules are pulled away from one another and cavities or bubbles are formed in a process called cavitation. The bubble continues to absorb energy until it can no longer sustain itself and then implodes, producing intense focused shearing forces, which rupture cell walls.

It is also known to use 20 kHz ultrasound waves for fragmenting DNA, which frequency is believed to provide for shorter treatment times (Mann T L, Krull U J, "The application of ultrasound as a rapid method to provide DNA fragments suitable for detection by DNA biosensors", Biosensors and Bioelectronics, Vol. 20, 2004, pp. 945-955; Rageh M. M., El-Lakkani A., et al., "Effect of high power ultrasound on aqueous solution of DNA", International Journal of Physical Sciences, Vol. 4, 2009, pp. 63-68).

Other apparatuses work with much higher frequencies in the MHz range (see e.g. U.S. Pat. No. 6,719,449).

Apparatuses for ultrasound shearing are known to be configured to perform different kinds of operations (cell lysis, DNA shearing, chromatin shearing). For each application, a number of specific usage protocols have been determined. These may include selecting the size of the sample, the periodicity of activation of the ultrasound waves and duty cycle, and the total duration of treatment.

One apparatus suitable for DNA fragmentation by ultrasound is commercialised by the Assignee under the name Bioruptor® (Diagenode, Belgium). Samples of DNA or chromatin are suspended in a liquid solution in a sample tube. The sample tube is suspended in a tank filled with a liquid medium (typically water). Ultrasound wave transducers are coupled to the bottom wall of the tank. Upon activation of the transducers, ultrasound waves having a frequency of 20 kHz are generated at the bottom wall of the tank, and propagate through the liquid medium to the sample tube. From the sample tube, the ultrasound waves are transmitted to its content, which then experiences mechanical stresses as indicated above. In the DNA sequence fragments, the double stranded (ds) DNA recovery is low.

In an article entitled "Specificity of DNA Cleavage by Ultrasound", Molecular Biology, 2006, Vol. 40 No. 2, pp. 276-283, Grokhovsky analyses cleavage of DNA fragments having a starting size of 439-475 bp in 0.2 ml sample tubes at a concentration of 5-10 µg/ml using ultrasound at 44 kHz and 22 kHz, but does not see any effect between the two frequencies.

In an article entitled "Development of a fast and efficient ultrasonic-based strategy for DNA fragmentation", Talanta 81 (2010), pp. 881-886, Larguinho et al evaluate several ultrasound-based platforms for DNA sample preparation. They found that a device referred to as the Sonoreactor UTR200, Heilscher Ultrasound Tech working at 24 kHz showed the best efficiency of DNA fragmentation and was considered the best ultrasonic tool to achieve effective DNA fragmentation at high throughput. An ultrasonic bath was found to have a low intensity of sonication with consequently a cavitation efficiency which is insufficient for promoting considerable DNA fragmentation.

Document WO 93/03150 concerns DNA fragmentation using a frequency of 60 kHz. The document describes to perform the ultrasonic treatment similar to what is explained in EP 0337690. In the latter document, ultrasound treatment is effected based on application of an ultrasonic tip to the wall of a cuvette.

Since fragmented DNA is increasingly being used in the preparation of sequencing libraries, there is an increased need of providing DNA fragments of predetermined size and with as little variance (spread) on the size as possible. Due to the increasing demand for fragmented DNA, there also exists a need of improving the cost-effectiveness of DNA fragmentation, and hence increasing the useable fraction of the fragmented DNA and increasing throughput times of DNA fragmentation processes by reducing fragmentation time.

The present invention therefore aims to provide methods and apparatuses that allow to obviate drawbacks of the prior art.

In particular, it is an aim of the invention to provide methods and apparatuses enabling to fragment DNA so that fragments with a small variance/standard deviation in size are obtained.

It is an aim of the invention to provide methods and apparatuses enabling to fragment RNA as well.

It is also an aim of the invention to provide methods and apparatuses which enable to improve the cost-effectiveness of fragmenting DNA.

It is also an aim of the invention to provide methods and apparatuses which enable to decrease the time needed for fragmenting DNA and increase the throughput.

It is also an aim of the invention to provide methods and apparatuses which enable to augment dsDNA recovery in DNA sequence fragments.

According to an aspect of the invention, there is provided a method of fragmenting a DNA sequence into fragments of smaller size as set out in the appended claims. The DNA sequence is suspended in a solution, which can be liquid or gel-like, and is subjected to the action of ultrasound waves so as to shear the DNA.

According to the invention, the ultrasound waves have a frequency as indicated in the appended claims. The inventors found that using such a frequency enables to obtain smaller size distributions for the obtained fragments, to reduce the time required for obtaining such fragments and to use lower ultrasound power intensities for shearing as compared to the known frequency of about 20 kHz. This results not only in an increased usefulness of DNA shearing methods of the invention for sequencing applications, but also allows reducing costs.

Further aspects of the invention are set out in the appended dependent claims.

According to another aspect of the invention, there is provided an apparatus for use in methods of the invention, as set out in the appended claims.

BRIEF DESCRIPTION OF THE DRAWINGS

FIG. 9A represents a gel electrophoresis of total RNA dissolved in 100 µl samples and sonicated for a varying duration as indicated in Example 7. FIG. 9B shows an electropherogram corresponding to lane 4 of FIG. 9A. FIG. 9C shows an electropherogram corresponding to lane 5 of FIG. 9A.

DETAILED DESCRIPTION OF THE INVENTION

Aspects of the invention relate to the fragmentation of DNA sequence into DNA sequence fragments of smaller size. The starting material is genomic or plasmid DNA, or DNA with a size larger than or equal to 10000 base pair (bp), advantageously larger than or equal to 25000 bp.

Aspects of the invention relate equally to fragmentation of RNA sequence into RNA sequence fragments. It will be convenient to note that where in the present description fragmentation of DNA sequences are described, same methods and apparatuses are understood to apply to RNA fragmentation as well.

Methods of the invention are arranged to fragment such sequence into fragments having a mean size smaller than or equal to 5000 bp, preferably smaller than or equal to 2000 bp, preferably smaller than or equal to 1300 bp, preferably smaller than or equal to 1075 bp, preferably smaller than or equal to 800 bp, preferably smaller than or equal to 400 bp, preferably smaller than or equal to 275 bp, preferably smaller than or equal to 175 bp. The mean size of the obtained sequence fragments is preferably larger than or equal to 50 bp, preferably larger than or equal to 100 bp. Indicated upper and lower size limits can be combined to yield optimal size ranges.

Fragmentation is effected by shearing using ultrasound waves. According to an aspect of the invention, ultrasound waves having a frequency larger than or equal to about 28 kHz, advantageously larger than or equal to about 32 kHz, advantageously larger than or equal to about 35 kHz, advantageously larger than or equal to about 36 kHz advantageously larger than or equal to about 37 kHz, and smaller than or equal to about 80 kHz, advantageously smaller than or equal to about 60 kHz, advantageously smaller than or equal to about 50 kHz, advantageously smaller than or equal to about 48 kHz, advantageously smaller than or equal to about 45 kHz and advantageously smaller than or equal to about 43 kHz are used. Indicated upper and lower frequency limits can be combined to yield optimal frequency ranges.

Alternatively, ultrasound waves having a frequency larger than or equal to about 45 kHz, advantageously larger than or equal to about 49 kHz, and smaller than or equal to about 80 kHz, advantageously smaller than or equal to about 60 kHz can be used, wherein indicated upper and lower frequency limits can be combined.

Such ultrasound waves can be generated by known transducers, such as piezoelectric or magnetostrictive transducers. Excitation of the DNA sequence by the ultrasound waves is advantageously indirect, in that the ultrasound waves are generated at a remote location and are made to propagate through one or more media before arriving at the sequence. Indirect excitation can cause a gentler excitation of the sequence, so that more consistent fragments are obtained.

Figure 1:
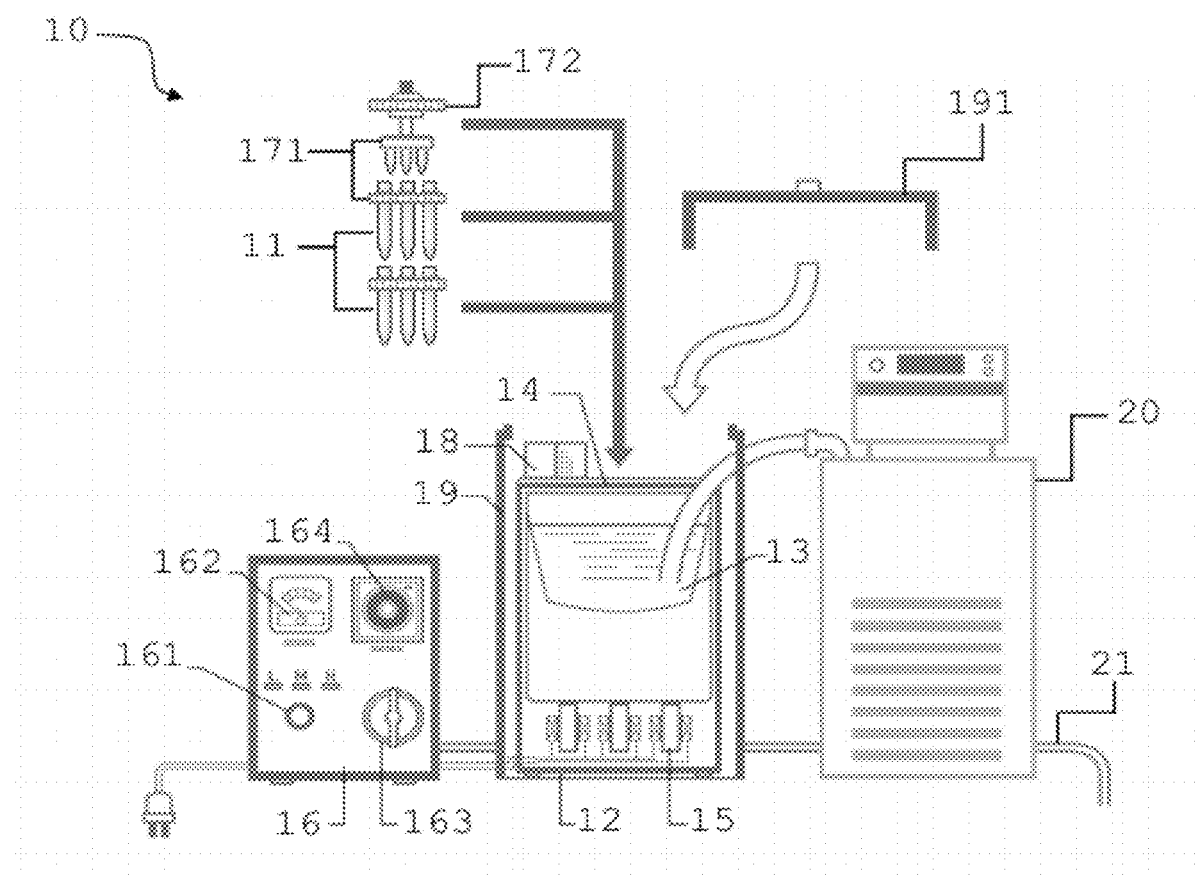
FIG. 1 represents an apparatus for DNA shearing using ultrasound waves according to the invention.

Referring to FIG. 1, there is provided an apparatus 10 capable of subjecting a DNA sequence-comprising solution to ultrasound waves in accordance with aspects of the present invention. Such a solution can be liquid or gel-like as is known in the art. The apparatus of FIG. 10 is constructionally similar to apparatuses as described in U.S. Pat. No. 4,874,137, which reference is incorporated herein by reference.

In apparatus 10, the DNA sequence-comprising solution (sample) is provided in a container, preferably a sample tube 11.

Container 11 and the solution are excited indirectly by the ultrasound waves. The apparatus therefore comprises a main body 12 which holds a tank 13 configured for containing a liquid, preferably water. Container 11 keeps the solution isolated from the medium (water) within the tank 13.

The tank 13 may be closed by a lid 14 which is configured for keeping the sample tube 11 suspended in the tank 13.

One or more ultrasound wave generators (transducers) 15 are coupled externally to the tank 13, preferably underneath the bottom of tank 13. Transducers 15 can be of the magnetostrictive type and are configured to generate mechanical vibrations, having a frequency as indicated, and which are transmitted to the tank 13. For operation, tank 13 is filled with a liquid. A drain pipe 21 may be provided to drain the liquid from tank 13 after operation. The mechanical vibrations of the tank 13 propagate through the liquid in the form of pressure (ultrasound) waves of same frequency.

In operation, the sample tube 11 is suspended (or baths) in the liquid within tank 13, so that the tube 11 is subjected to the action of the ultrasound (pressure) waves propagating through the liquid and vibrates.

Sample tubes made of polypropylene, polymethylpentene or polycarbonate can be used. It has been observed that a sample tube made of polypropylene gives better results.

It is preferred that the sample tube 11 is so suspended in the liquid of tank 13 that the liquid level of the DNA sequence-comprising solution in sample tube 11 is lower than the level of the liquid in tank 13.

Preferably, sample tubes 11 tapering towards the bottom end are used. The sample tubes 11 are advantageously sized to contain a maximal volume larger than or equal to about 0.1 ml, advantageously larger than or equal to about 0.25 ml, advantageously larger than or equal to about 0.4 ml. The sample tube size is advantageously smaller than or equal to about 10 ml, advantageously smaller than or equal to about 5 ml, advantageously smaller than or equal to about 2 ml, advantageously smaller than or equal to about 1 ml.

Transducers 15 are electrically connectable to a control and power supply unit 16, which can be configured for controlling the frequency of excitation, the power, duration and any other settable parameter relating to the generation of the ultrasound waves.

Control unit 16 is advantageously provided with a human interface panel, on which one or more of the above indicated parameters can be set. By way of example, control unit 16 can be provided with a control knob 161 for setting the output power of the generated ultrasound waves. The output power may be visualized on an intensity level indicator 162. Transducers 15 advantageously have a total (input) power in the range between about 10 W and about 350 W, advantageously between about 10 W and about 200 W. This corresponds to a power intensity (in the liquid of tank 13) of between about 0.25 W/m$^2$ and about 8.75 W/m$^2$, advantageously between about 0.25 W/m$^2$ and about 5 W/m$^2$. It is to be noted that there is a significant difference between the theoretical power delivered by the transducer and the actual power dissipated in the liquid in tank 13, see A. W. Davis and D. R. Phillips, "A Defined Molecular-Weight Distribution of Deoxyribonucleic Acid after Extensive Sonication", Biochem. J. (1978) 173, pp. 179-183).

Control unit 16 and/or transducers 15 may be configured to generate ultrasound waves of a single fixed frequency, not selectable by an operator.

The duration of treatment can be set with a timer 163. Possible durations fall in the range between about 30 s and about 100 minutes, advantageously between about 30 s and about 60 minutes. The duration refers to the total time of treatment, including non-active periods in case of intermittent (cyclic) operation.

Figure 2:
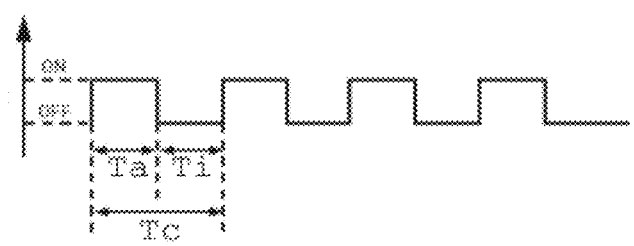
FIG. 2 represents a plot of intermittent (cyclic) generation of ultrasound waves.

In addition, the control unit can be provided with a selector 164 for selecting intermittent generation of ultrasound waves. Transducers 15 can be configured to operate intermittently, such as in (equal) cycles formed of an active period (Ta) wherein the transducers are active and generate ultrasound waves and an inactive period (Ti) wherein the transducers are not active and do not generate ultrasound waves, as illustrated in FIG. 2.

The sum of the active and inactive time periods within a single cycle is referred to as the cycle period Tc. The ratio of active period Ta to the cycle period Tc is referred to as the duty cycle.

Possible cycle periods are longer than or equal to about 2 s, advantageously longer than or equal to about 4 s, advantageously longer than or equal to about 8 s. They may be shorter than or equal to about 6 minutes (360 s), advantageously shorter than or equal to about 3 minutes (180 s), advantageously shorter than or equal to about 2 minutes (120 s). Possible duty cycles fall in the range between about 0.1 (10%) and about 0.8 (80%), advantageously between about 0.2 and about 0.7, advantageously between about 0.3 and about 0.7.

DNA Total cycle number may vary between 1 and 100.

Advantageously, a holder 171 for simultaneously suspending a plurality of sample tubes 11 from lid 14 can be provided. This has the advantage that a plurality of DNA sequence samples can be treated (fragmented) simultaneously, which increases throughput. Holder 171 can be connected to a gear wheel 172 for coupling to a motor 18 enabling to rotate the holder 171 during operation.

Main body 12 is advantageously placed in a soundproof box 19 for acoustic isolation. Box 19 can be provided with a closing soundproof lid 191.

For optimized treatment, the solution should preferably be maintained at temperatures between about 4° C. and about 10° C., even during treatment. Since ultrasound excitation causes a temperature increase, apparatus 10 preferably comprises a temperature control unit (cooling unit) 20 configured for maintaining the solution at a predetermined temperature. One way of effecting temperature control is to keep the liquid of tank 13 cooled, as illustrated in FIG. 1.

Apparatuses as described hereinabove can be advantageously used to carry out methods of the invention. In order to carry out such methods, the starting sequence should be suitably conditioned. This can comprise an extraction and purification step of the DNA sequence from a biological sample containing DNA, such as a cell or a tissue and dissolving the obtained DNA sequence in a sonication buffer, such as a TE buffer (Tris-EDTA buffer) having a pH in the range between about 7.5 and about 8.0. Other conditioning steps, such as adding to the DNA-containing solution a solid support, an organic solution, a detergent, a positively charged polymer, or organic molecules may be of interest.

The DNA concentration in the sonication buffer advantageously falls in the range between about 0.001 µg/µl and about 0.5 µg/µl, advantageously between about 0.001 µg/µl and about 0.25 µg/µl, advantageously between about 0.001 µg/µl and about 0.1 µg/µl.

Of the DNA sequence-containing solution, a volume advantageously smaller than or equal to 500 µl, advantageously smaller than or equal to 400 µl, advantageously smaller than or equal to 300 µl, advantageously smaller than or equal to 250 µl, advantageously smaller than or equal to 150 µl is put in a container, such as a sample tube 11, which can have sizes as indicated. A volume of DNA sequence-containing solution of at least 1 µl is advantageously used, advantageously at least 10 µl.

The container with isolated volume of DNA sequence-containing solution is then subjected to the action of ultrasound waves of frequency as indicated.

One or more protocols may be set up for carrying out shearing/fragmenting treatment according to the invention in order to obtain DNA sequence fragments of desired (mean) size, such as mean sizes as indicated hereinabove and with narrow size distributions. Methods of the invention enable to fragment the DNA sequence into fragments of smaller size and having a size distribution with a coefficient of variance advantageously smaller than 15%, advantageously smaller than 12%.

The protocol may include a selection of the frequency of the ultrasound waves. Frequency may be dependent on (or determined by) the apparatus used.

The protocol may include a selection of the power or energy intensity of the ultrasound waves.

The protocol may include a selection of the duration of the treatment and/or periodicity (intermittent or continuous) of the treatment. Preferred values for duration and periodicity are as indicated hereinabove.

Methods of the invention can be used with any type of double stranded DNA can be used, from plasmid DNA or synthetic dscDNA to large genomic DNA. The DNA can be obtained from various species such as Human, Mouse, Rat, Loris (Strepsirrhine primate), Lemur, Chimpanzee, Xenopus Laevis, bacteria such as *E. coli*, yeast, etc.

DNA fragments as obtained through methods of the invention are advantageously used for the creation of genomic libraries for further DNA sequencing applications. Therefore, the method and apparatus according to the invention can be combined with complementary DNA sequencing methods and apparatus. DNA fragments as obtained through methods of the invention may as well find application in adapting material properties, such as in polymers and carbon nanotubes.

EXAMPLE 1

DNA Fragmentation at 38.5-41.5 kHz

Sample preparation: For each test sample, 1 µg human genomic DNA (Coriell Cell Repositories, NA 18507) was dissolved in 100 µl TE buffer (10 mM Tris, 1 mM EDTA, pH 8.0). A volume of 100 µl of the solution was put in a Costar® 0.65 ml Low Binding Microcentrifuge Tube (Cat. no. 3206). The sample is vortexed gently during 10 sec and then centrifuged for 10 sec to collect the sample at the bottom of the tube before being subjected to ultrasound waves.

Setup: an apparatus as represented in FIG. 1 is used, having a tank filled with about 750 ml of water. The sample tube with DNA buffer is placed in a holder and suspended in the water, such that the buffer level in the sample tube lies below the water level in the tank. The water in the tank is maintained at 4° C. using a cooling unit. Magnetostrictive transducers are coupled to the bottom of the tank and are configured for oscillating at 40 kHz±1.5 kHz (measured at 38.5-41.5 kHz) with total (input) power of about 150W. Transducers were activated intermittently using cycles of 10 s ON/30 s OFF or 30 s ON/30 s OFF (indicated for each test result).

All test results are analysed using an Agilent 2100 Bioanalyzer with High Sensitivity DNA chip.

Figure 3:
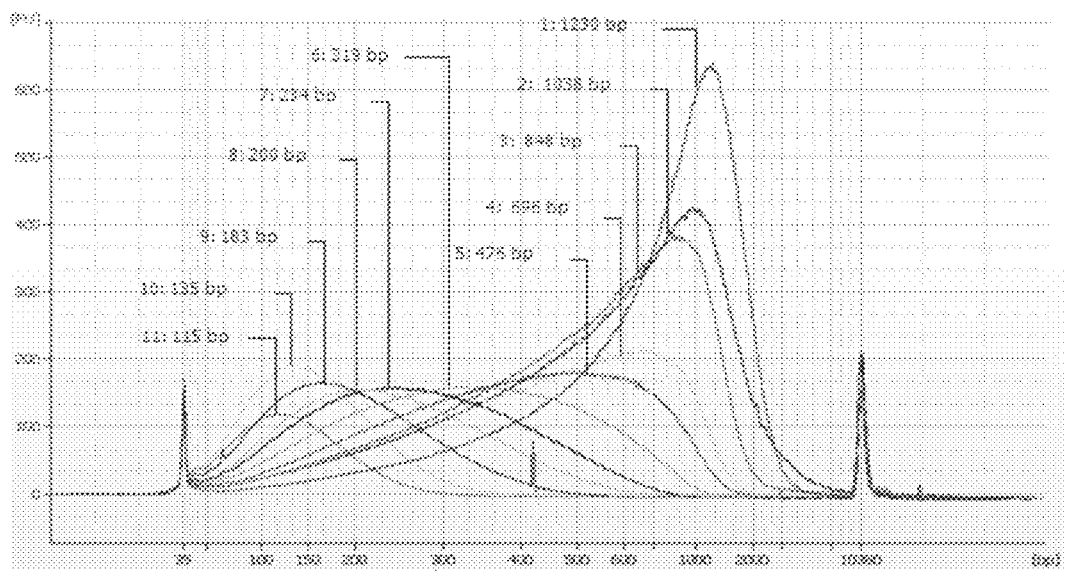
FIG. 3 represents a graph of the size distribution of DNA sequence fragments as obtained in example 1 described below. Size distribution (in base-pair) is plotted versus Fluorescence Units (FU).

Eleven test samples (referenced with consecutive Arabic numerals) were exposed to ultrasound waves as indicated, but under different cycle conditions (number of cycles, duration). Obtained test results are summarized in table 1 and are plotted in FIG. 3. As is evident from table 1, a longer treatment duration is required for obtaining DNA fragments of smaller size. Also evident from table 1 is the high dsDNA recovery in DNA sequence fragments, for example: about 90% dsDNA recovery for DNA sequence fragments of about 1000 bp and about 50% dsDNA recovery for DNA sequence fragments of about 100 bp. The dsDNA was quantified using an intercalating dye exhibiting a higher specificity for double stranded DNA, for example SYBR® Green dye. Longer sonication times (i.e. higher treatment duration) induce more degradation of ds DNA and generate smaller fragments, more single stranded (ss) DNA and more single strand breaks. The lower the power and/or the lower the treatment duration, the higher the percentage of dsDNA recovery in the DNA sequence fragments.

EXAMPLE 2

Run-to-Run Variation

Figure 4:
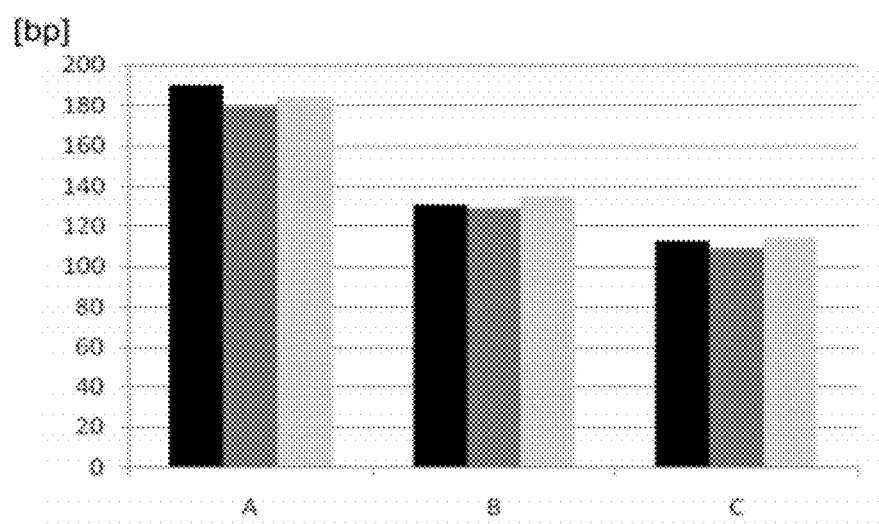
FIG. 4 represents a graph of the mean size variation between different runs (under same conditions) of DNA sequence fragments obtained with example 2, for three different treatment durations (A: 15 minutes, B: 40 minutes, C: 60 minutes). Y-axis corresponds to the size of DNA fragments in base pair.

FIG. 4 plots the run-to-run variation of the average size of sheared DNA fragments obtained with three experiments with same settings and duration of treatment in same apparatus as in example 1 (A: 15 minutes, B: 40 minutes, C: 60 minutes total duration). Standard conditions were used in each case (30 s/30 s cycles (50% duty cycle), Low power setting or 150 W), human Genomic DNA (Cell Repositories, NA18507), 0.65 ml sample tubes. Samples were analysed on Bioanalyzer 2100 with High Sensitivity DNA chips.

TABLE 1

Example 1 test results (bp = base pair, SD = standard deviation, CV = coefficient of variation (%), ' = minutes).

| No. | Time/ cycles | Mean size (bp) | | | peak width at ½ height | | peak width at ¼ height | | double-stranded DNA recovery (%) | | |
|---|---|---|---|---|---|---|---|---|---|---|---|
| | | mean | SD | CV | Max | Min | Max | Min | mean | SD | CV |
| 1 | 2 cycles 10/30 | 1230 | 67.3 | 5.7 | 1179 | 720 | 1562 | 903 | 91.3 | 2.5 | 2.7 |
| 2 | 3 cycles 10/30 | 1038 | 32.8 | 3.4 | 1588 | 493 | 1387 | 683 | 95.4 | 8.7 | 9.1 |
| 3 | 4 cycles 10/30 | 848 | 49.7 | 5.9 | 1240 | 455 | 1078 | 619 | 89.4 | 2.3 | 2.5 |
| 4 | 2' 30/30 | 676 | 77.4 | 10.7 | 953 | 402 | 832 | 517 | 85.5 | 2.5 | 2.9 |
| 5 | 3' 30/30 | 476 | 33.4 | 7.2 | 635 | 311 | 564 | 393 | 82.2 | 4.0 | 4.8 |
| 6 | 5' 30/30 | 319 | 27.6 | 8.7 | 426 | 211 | 373 | 270 | 81 | 4.9 | 6.0 |
| 7 | 7' 30/30 | 234 | 23.4 | 9.1 | 323 | 150 | 272 | 188 | 76.1 | 5.5 | 7.2 |
| 8 | 10' 30/30 | 200 | 11.1 | 5.2 | 277 | 121 | 236 | 165 | 73.4 | 5.8 | 7.9 |
| 9 | 15' 30/30 | 183 | 10.5 | 5.7 | 207 | 98 | 179 | 126 | 67.1 | 5.5 | 8.2 |
| 10 | 40' 30/30 | 135 | 5.2 | 3.9 | 171 | 86 | 151 | 111 | 52.7 | 8.0 | 15.3 |
| 11 | 60' 30/30 | 115 | 5.0 | 4.5 | 151 | 77 | 134 | 97 | 48.1 | 5.3 | 13.9 |

COMPARATIVE EXAMPLE 3

DNA Fragmentation at 20 kHz and 40 kHz

Table 2 shows comparative data of sonication time required for fragmenting a same starting DNA sequence into fragments of indicated target size. It can be clearly deduced from the table that the reduction in sonication time is more significant for smaller fragment sizes (at least 50% reduction in sonication time for fragments of 700 bp or smaller).

TABLE 2

Comparative data for effective sonication time (total active sonication time, excluding inactive periods) for fragmenting a DNA sequence into a target fragment size

| Target size | Total sonication (active time only) time at 40 kHz | Total sonication (active time only) time at 20 kHz |
|---|---|---|
| 150 bp | 15 min | 45 min |
| 200 bp | 6 min 30 s | 30 min |
| 350 bp | 2 min 15 s | 5 min |
| 450 bp | 1 min 30 s | 3 min |
| 700 bp | 1 min | 2 min |
| 900 bp | 45 s | 1 min |
| 1250 bp | 20 s | 30 s |

COMPARATIVE EXAMPLE 4

DNA Fragmentation at 20 kHz and 40 kHz

To compare the DNA shearing efficiency at the two frequencies, samples were prepared under the following conditions. An apparatus as used in example 1 is used for the 40 kHz experiments. An apparatus with similar construction, but producing 20 kHz ultrasound waves is used for the 20 kHz experiments. In both cases, a 12×0.65-ml sample tube holder was used for maintaining 0.65 ml Low Binding tubes (Costar, Ref. 3206) in the water bath. Human genomic DNA was used as template and samples are prepared as in Example 1, but now with a TE buffer of 7.6 pH. The starting size of the DNA fragments in the samples was larger than 50000 bp. All samples were analyzed on a Bioanalyzer 2100 using DNA High Sensitivity chip (1 µl loaded per sample).

Figure 5A:
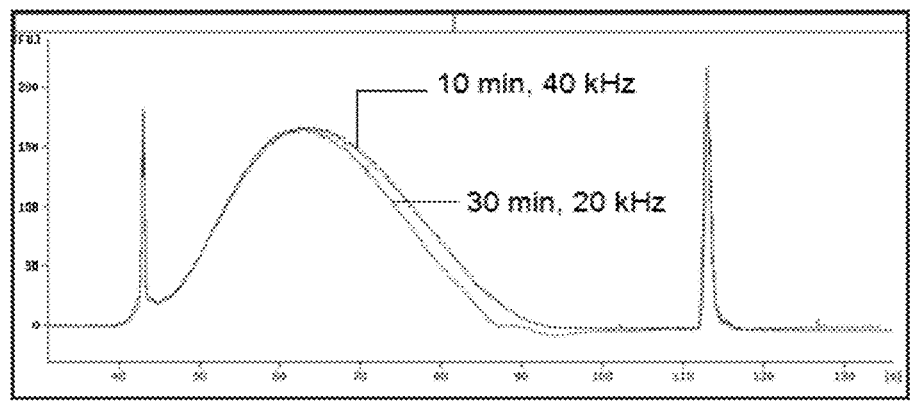
FIG. 5A-C represents comparative electropherograms of DNA fragments obtained after sonication at 40 kHz and at 20 kHz as described in Example 4.

The samples were loaded in the apparatuses and ultrasound treatment was performed at maximum power (150 W) using 30 s On-30 s Off cycles (cycle duration 1 minute, duty cycle 0.5). Sonication time was selected in function of to-obtain fragment size FIGS. 5 A-C show a comparison of the obtained DNA size distributions after sonication. FIG. 5A compares obtained fragment sizes of 200 bp mean size. Methods and apparatuses of the invention only require 10 minutes of total sonication treatment to obtain DNA fragments of 200 bp, whereas at 20 kHz one would need 30 minutes to obtain fragments of same size. This means a time saving of 20 minutes or 66% compared to prior art procedures.

Figure 5B:
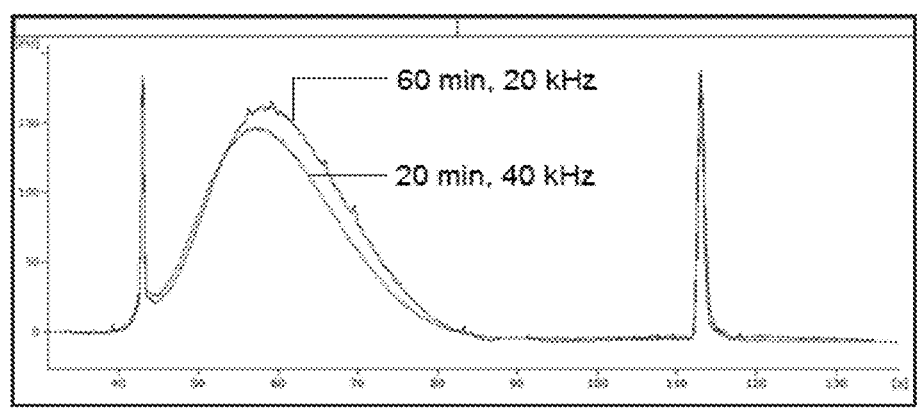

FIG. 5B compares obtained fragment sizes of 135 bp mean size. Methods and apparatuses of the invention only require 20 minutes of total sonication treatment to obtain DNA fragments of 135 bp, whereas at 20 kHz one would need 60 minutes to obtain fragments of same size. This means a time saving of 40 minutes or 66% compared to prior art procedures.

Figure 5C:
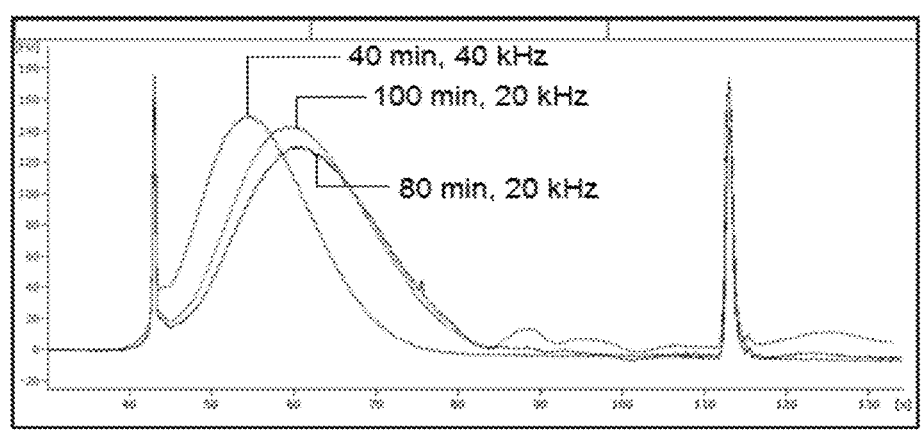

FIG. 5C compares obtained fragment sizes of 115 bp mean size. Methods and apparatuses of the invention only require 40 minutes of total sonication treatment to obtain DNA fragments of 115 bp, whereas at 20 kHz one would need 80 to 100 minutes to obtain fragments of same size. This means a time saving of 50% and more compared to prior art procedures.

EXAMPLE 5

Impact of DNA Sample Concentration on Sonication Performance

In the present experiment the influence of DNA concentration in the test samples subjected to sonication was tested. A same sonication apparatus as used in example 1 (and described with reference to FIG. 1) and configured to generate 40 kHz ultrasound waves was used. The water bath was maintained at 4° C. It was equipped with a 12×0.65-ml tube holder, holding 0.65 ml Low Binding sample tubes (Costar, Ref. 3206).

Human genomic DNA (starting concentration: 0.373 µg/µl, source: Coriell Cell Repositories) was used as template for preparing the samples. Samples with three different DNA fragment concentrations (0.2 µg/100 µl, 1 µg/100 µl, and 5 µg/100 µl) were prepared in a TE buffer (pH 7.6) solution. All samples had a same volume of 100 µl, and each sample was put in a 0.65 ml sample tube. The starting size of the DNA in the samples was higher than 50000 bp.

Four samples were sonicated per experiment (of same DNA concentration). Each experiment was repeated three times for each concentration and consisted in subjecting the samples to 40 cycles 30 s On, 30 s Off (40 min sonication, 50% duty cycle).

Figure 6A:
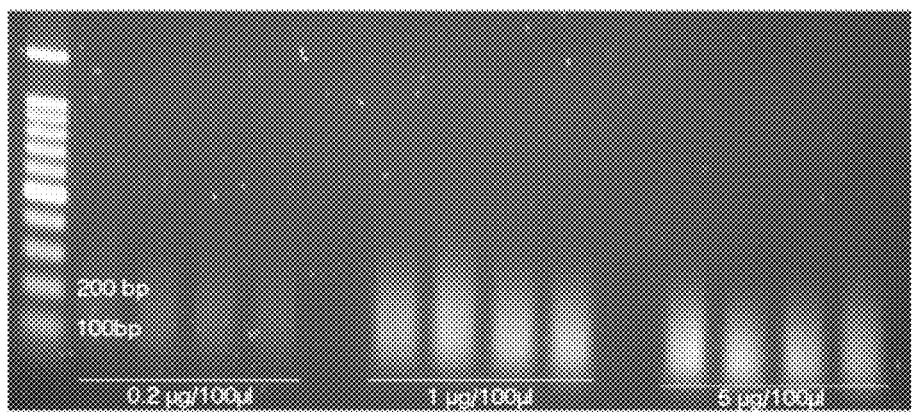
FIGS. 6A-C represent agarose gel electrophoresis results of sonicated samples comprising DNA fragments in differing concentrations according to Example 5. Each figure (A-C) shows results of different runs.
Figure 6B:
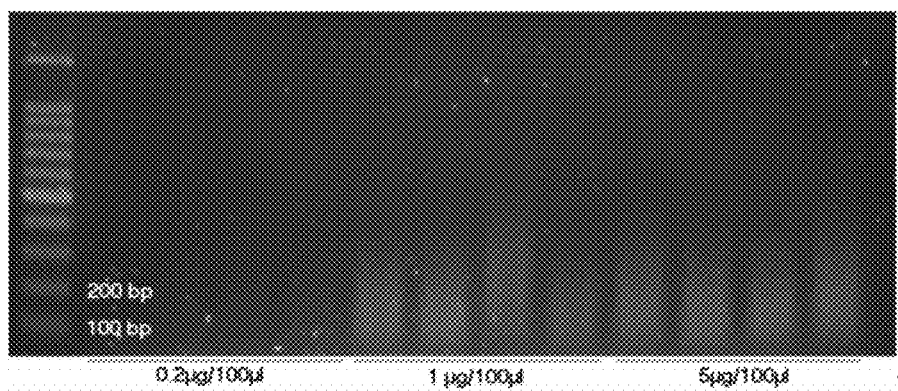
Figure 6C:
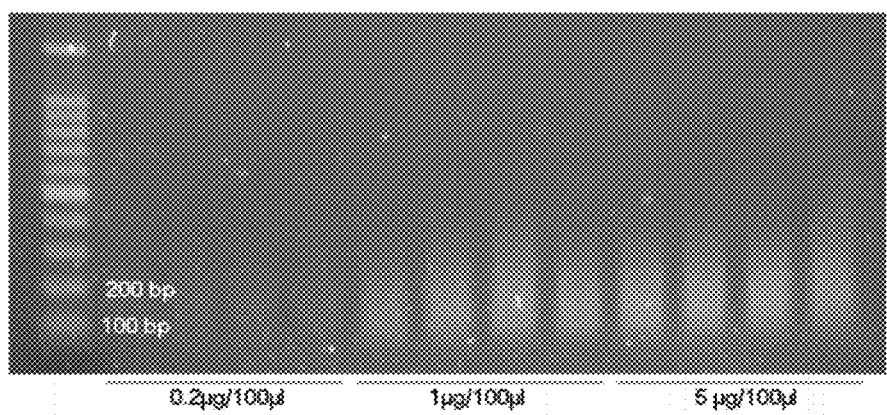

The fragmented DNA samples were analyzed on 1% agarose or on a Bioanalyzer 2100 High Sensitivity DNA chip and the results are shown in FIG. 6A-C for 15 µl of sheared DNA loaded on 1% agarose gel (MW ladder—Small Size). FIG. 6 A shows results of the first run for each concentration. FIGS. 6 B and C show results of the second and third runs respectively for same concentrations.

Figure 7:
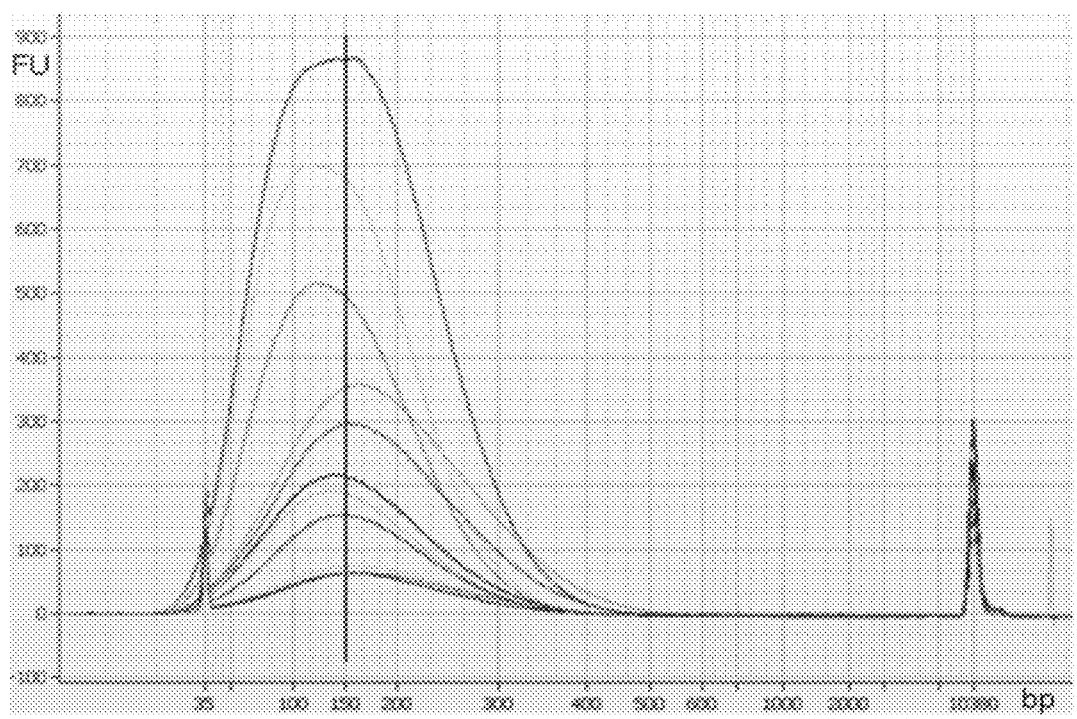
FIG. 7 represents an electropherogram of 11 out of the 12 samples of FIG. 6A.

The results shown in FIG. 6A are represented in the electropherogram of FIG. 7 as well. FIG. 7 shows 11 out of the 12 samples represented in FIG. 6A and was obtained by loading 1 µl of each sheared sample on the Bioanalyzer High Sensitivity DNA. The target DNA fragment size after sonication was 150 base pair. The observed average peak size was 142 bp with a CV=8.9%. The results hence were seen to correlate with the expected target size irrespective of the DNA concentration of the samples. Therefore, fragmentation methods according to the invention work equally well for samples with DNA concentration in the tested range between 0.2 µg and 5 µg/100 µl final volume.

EXAMPLE 6

Impact of Sample Volume on DNA Fragmentation Performance

Experiments were carried out with sample tubes filled with different quantities of DNA solutions. Experiments were carried out in a same apparatus as for Example 5, having a 12×0.65-ml tube holder. 0.65 ml Low Binding sample tubes (Costar, Ref. 3206) were used for the experiments.

Human genomic DNA (starting concentration: 0.204 µg/µl, source: Promega) was used as template for preparing the samples. Samples were prepared based on a TE buffer of pH 7.6. First samples were prepared with a DNA concentration of 0.03 µg/µl and a final sample volume of 50 µl. Second samples were prepared with a DNA concentration of 0.01 µg/µl and a final sample volume of 100 µl. Each sample was put in a 0.65 ml sample tube as indicated above. The starting size of the DNA sequence in the samples was higher than 50000 bp.

Figure 8A:
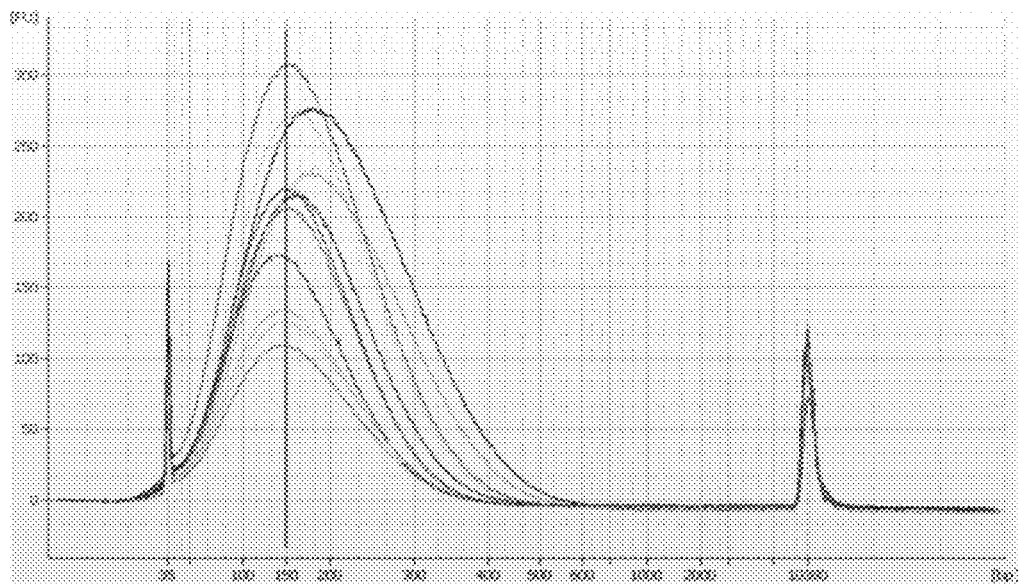
FIGS. 8A-B represent electrophoresis results of DNA fragmentation in samples of 50 µl and 100 µl volume in accordance with Example 6.
Figure 8B:
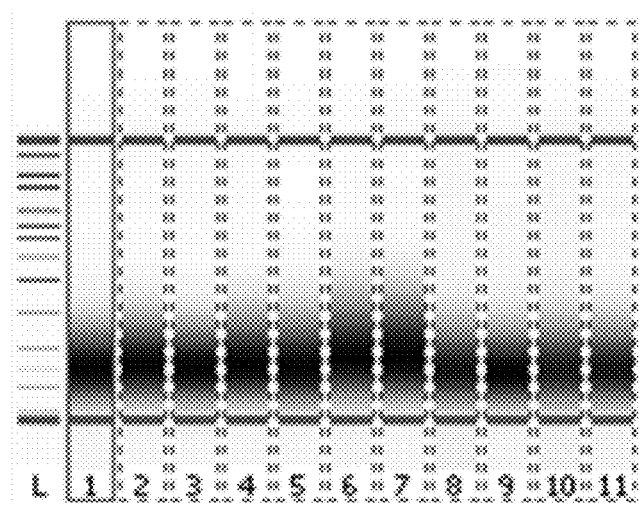

A total of 12 samples (6 of 50 µl and 6 of 100 µl) were prepared and subjected to sonication under same conditions as indicated in Example 5 (40 cycles, 30 s On, 30 Off). The samples were analyzed by loading 1 µl on a Bioanalyzer High Sensitivity DNA chip after sonication treatment. FIG. 8A-B show electrophoresis results for 11 out of the 12 samples. The target size was 150 base pair. The observed average peak sizes correlate very well with the expected target size irrespective of the sample volume used. The 50 µl sample volumes had an average fragment size of 159.7 bp with CV=8.3%; the 100 µl sample volume had an average fragment size of 145 bp with CV=2.54%. This means that sample volume variations do not negatively affect performance of methods of the invention.

RNA Fragmentation

EXAMPLE 7

Methods of the invention can also be used for fragmenting RNA sequences in same manner as with DNA sequences as described above. Experiments were conducted with total RNA sequences which were dissolved in a TE buffer (10 mM Tris, 1 mM EDTA, pH 7.5-8.0) which was RNase free. Samples of dissolved RNA were prepared in volumes of 100 µl with a RNA concentration of 0.05 µg/µl, which were put in 0.65 ml sample tubes. The RNA sequences had a starting size larger than 50000 bp. Same sample tubes and apparatus as with Examples 5 and 6 above were used.

The samples were briefly vortexed and centrifuged for 10 s before starting sonication. In addition, short centrifugation steps after every five sonication cycles were performed. Sonication was performed with 30 s On/30 s Off-cycles at high power (150 W). Total number of cycles depended on target RNA fragment size. The samples were subsequently analysed on Biorad Experion using Eukaryote Total RNA HighSens chip. Results are presented in FIG. 9, showing different RNA size distributions produced by varying the duration of sonication.

Figure 9A:
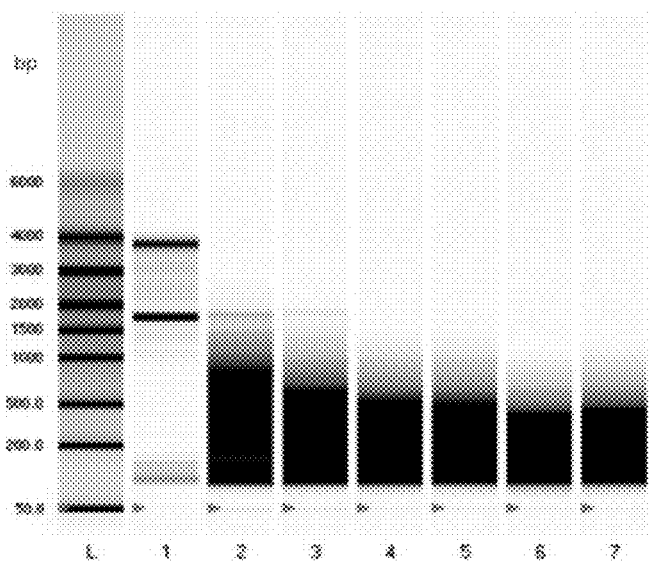
FIGS. 9A-C represent electrophoresis results of total RNA fragmentation according to the invention.

FIG. 9A shows duplicate profiles produced after 5 minutes (5 cycles) (lanes 2-3), 10 minutes (10 cycles) (lanes 4-5) and 15 minutes (15 cycles) (lanes 6-7) of sonication. Lane 1 shows the unfragmented total RNA (starting material). Lane L: Internal Molecular Weight Marker.

Figure 9B:
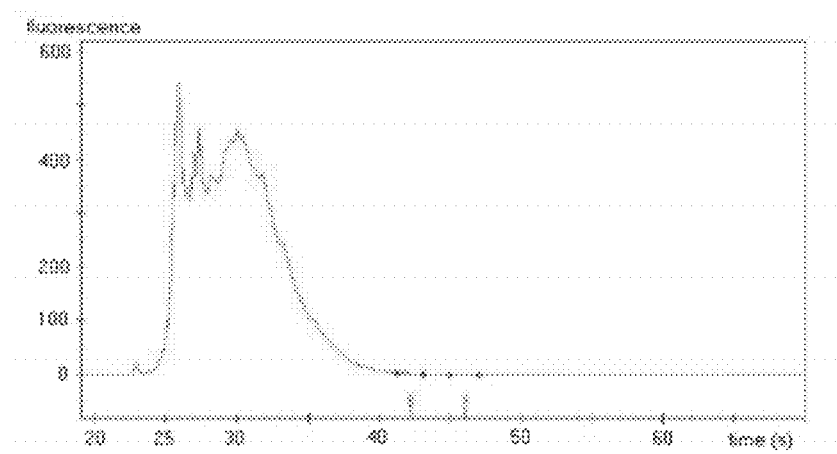
Figure 9C:
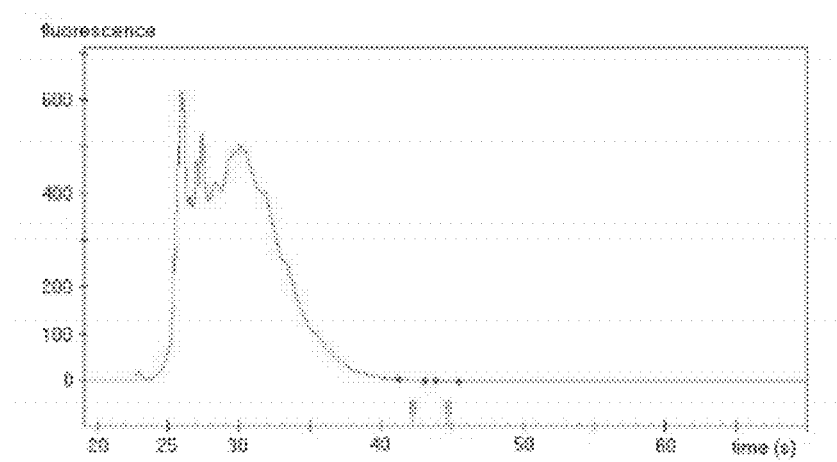

FIG. 9B-C compares the RNA size distributions of sheared total RNA of lanes 4 and 5 of FIG. 9A respectively. It can be seen that reproducibility of methods of the invention for fragmenting RNA is excellent.

The invention claimed is:

1. A method of fragmenting a DNA sequence having a size of at least 10000 base pair (bp) into fragments having a mean size between 100 bp and 400 bp with a coefficient of variation (CV) between 2.5% and 9.1%, the method comprising:
adding the DNA sequence to a buffer solution at a pH between 7.5 and 8.0 to obtain a solution comprising the DNA sequence, wherein the solution comprising the DNA sequence is put in a container;
placing the container in a liquid bath; and
subjecting the container in the liquid bath to the action of ultrasound waves such that the ultrasound waves travel through the liquid bath to excite the container and the solution comprising the DNA sequence so as to shear the DNA sequence, and wherein the ultrasound waves have a frequency falling in the range between 28 kHz and 80 kHz.

2. The method of claim 1, wherein the ultrasound waves have a frequency falling in the range between 36 and 50 kHz.

3. The method of claim 1, wherein the ultrasound waves have a frequency falling in. the range between 36 and 43 kHz.

4. The method of claim 1, wherein the solution comprising the DNA sequence has a volume smaller than or equal to 500 µl.

5. The method of claim 1, wherein the solution comprising the DNA sequence has a DNA concentration falling in the range between 0.001 µg/µl and 0.5 µl.

6. The method of claim 1, wherein the solution comprising the DNA sequence has a DNA concentration falling in the range between 0.001 µg/µl and 0.1 µg/µl.

7. The method of claim 1, wherein the solution comprising the DNA sequence is subjected intermittently to the ultrasound waves.

8. The method of claim 7, wherein the ultrasound waves are generated in cycles having a duration between 2 s and 360 s and a duty cycle between 10% and 80%.

9. The method of claim 1, wherein the container is a low binding, tube sized to contain a maximal volume between 0.1 ml and 10 ml.

10. The method of claim 1, wherein the container comprises multiple containers that are positioned at different locations in the liquid bath.

11. The method of claim 10, wherein the multiple containers are held in a support which is rotated relative to the liquid bath.

12. The method of claim 1 further comprising cooling the solution during application of the ultrasound waves.

13. The method of claim 1, wherein the liquid bath is contained in a tank and ultrasound transducers are externally coupled to the tank, and wherein subjecting the container in the liquid bath to the ultrasound waves is performed through excitation of the tank.

14. A method of fragmenting a DNA sequence having a size of at least 10000 base pair (bp) into fragments having a mean size between 400 bp and 800 bp with a coefficient of variation between 7.2% and 10.7%. the method comprising:
adding the DNA sequence to a buffer solution at a pH between 7.5 and 8.0 to obtain a solution comprising the DNA sequence wherein the solution comprising the DNA sequence is put in a container;
placing the container in a liquid bath; and
subjecting the container in the liquid bath to the action of ultrasound waves such that the ultrasound waves travel through the liquid bath to excite the container and the solution comprising the DNA sequence so as to shear the DNA sequence. and therein the ultrasound waves have a frequency failing in the range between 28 kHz and 80 kHz.

15. A method of fragmenting a DNA sequence having a size of at least 10000 base pair (bp) into fragments having a mean size between 800 bp and 1300 bp with a coefficient of variation between 3.4% and 5.9%. the method comprising:
adding the DNA sequence to a buffer solution at a pH between 7.5 and 8.0 to obtain a solution comprising the DNA sequence, wherein the solution comprising the DNA sequence is put in a container;
placing the container in a liquid bath; and
subjecting the container in the liquid bath to the action of ultrasound waves such that the ultrasound waves travel through the liquid bath to excite the container and the solution comprising the DNA sequence so as to shear the DNA sequence, and wherein the ultrasound waves have a frequency falling in the range between 28 kHz and 80 kHz.

16. The method of claim 14, wherein the container is a low binding tube sized to contain a maximal volume between 0.1 ml and 10 ml.

17. The method of claim 15, wherein the container is a low binding tube sized to contain a maximal volume between 0.1 ml and 10 ml.

18. The method of claim 14, wherein the ultrasound waves have a frequency falling in the range between 36 and 50 kHz.

19. The method of claim 15, wherein the ultrasound waves have a frequency falling in the range between 36 and 50 kHz.

20. The method of claim 14, wherein the liquid bath is contained in a tank and ultrasound transducers are externally coupled to the tank, and wherein subjecting the container in the liquid bath to the ultrasound waves is performed through excitation of the tank.

* * * * *